(12) United States Patent
Levy et al.

(10) Patent No.: US 11,813,173 B2
(45) Date of Patent: Nov. 14, 2023

(54) NON-EXPANDABLE MULTIPLE-SEGMENT LOCKABLE CAGE

(71) Applicant: CoreLink, LLC, St. Louis, MO (US)

(72) Inventors: Mark M. Levy, Raanana (IL); Eran Ishay, Tel Aviv (IL); Jaffar Hleihil, Jish (IL); Assaf Guy, Allone Abba (IL)

(73) Assignee: CORELINK, LLC, Fenton, MO (US)

( * ) Notice: Subject to any disclaimer, the term of this patent is extended or adjusted under 35 U.S.C. 154(b) by 0 days.

(21) Appl. No.: 16/158,128

(22) Filed: Oct. 11, 2018

(65) Prior Publication Data

US 2019/0091036 A1  Mar. 28, 2019

Related U.S. Application Data

(63) Continuation of application No. 15/440,113, filed on Feb. 23, 2017, now abandoned.

(51) Int. Cl.
*A61F 2/44* (2006.01)
*A61F 2/46* (2006.01)
*A61F 2/30* (2006.01)

(52) U.S. Cl.
CPC .......... *A61F 2/4425* (2013.01); *A61F 2/4455* (2013.01); *A61F 2/4611* (2013.01); *A61F 2002/30471* (2013.01); *A61F 2002/30507* (2013.01); *A61F 2002/30522* (2013.01); *A61F 2002/30523* (2013.01); *A61F 2002/30528* (2013.01); *A61F 2002/30538* (2013.01); *A61F 2002/30593* (2013.01); *A61F 2002/443* (2013.01); *A61F 2002/448* (2013.01)

(58) Field of Classification Search
CPC .............. A61F 2/44–447; A61F 2/4611; A61F 2002/443; A61F 2002/448
See application file for complete search history.

(56) References Cited

U.S. PATENT DOCUMENTS

| | | | |
|---|---|---|---|
| 6,993,808 B1 | 2/2006 | Bennett et al. | |
| 9,795,493 B1 | 10/2017 | Bannigan | |
| 2006/0189999 A1* | 8/2006 | Zwirkoski | A61F 2/442 606/90 |
| 2007/0225808 A1 | 9/2007 | Warnick | |
| 2008/0125865 A1 | 5/2008 | Abdelgany | |
| 2010/0249937 A1 | 9/2010 | Blain et al. | |
| 2013/0079883 A1 | 3/2013 | Butler et al. | |
| 2013/0184823 A1 | 7/2013 | Malberg | |
| 2015/0257894 A1 | 9/2015 | Levy et al. | |

\* cited by examiner

*Primary Examiner* — Nicholas J Plionis
(74) *Attorney, Agent, or Firm* — Stinson LLP

(57) ABSTRACT

A cage device includes first and second segments pivotally connected by a hinge. Pivoted movement of the segments with respect to each other is limited by a first stopper portion of the first segment abutting against a second stopper portion of the second segment.

9 Claims, 6 Drawing Sheets

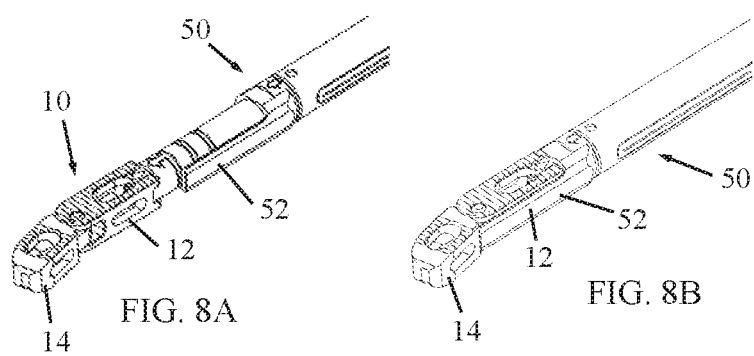
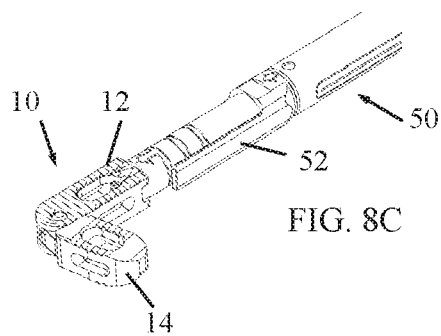
FIG. 8A
FIG. 8B
FIG. 8C

NON-EXPANDABLE MULTIPLE-SEGMENT LOCKABLE CAGE

FIELD OF THE INVENTION

The present invention generally relates to devices and methods for spinal fusion or other spinal techniques and particularly to a multiple-segment lockable cage for such spinal techniques.

BACKGROUND OF THE INVENTION

Cages for spine fusion are used to fuse two or more vertebrae for treatment of different pathologies. The cages improve the anterior column stability, preserve the disc space height, include chambers for bone graft that enhance the fusion process and are used in some cases with the addition of supplementary screws. The most efficient cages have a large contact surface for contacting both vertebrae endplates, superior and inferior, and are able to be located preferably in the periphery of the disc space.

Simple cages include a spacer of rectangular, circular or trapezoidal shape made of a single segment device. If one cage is insufficient to cover the space to be treated, more than one cage can be introduced into the space. Some cages have an expansion mechanism that allows them to expand in the space to provide increased coverage than in the initial position. Additional devices may include more than one segment attached together with hinges, pivots or turning points to be able to cover more of the vertebral surface with only one device. However, such devices suffer from a lack of manipulation control during the insertion process and while in the intervertebral space, including difficulty in locking the device in the final desired position.

SUMMARY OF THE INVENTION

The present invention seeks to provide a novel, simple articulated device, which includes two or more segments, which can be easily steered and locked in a desired orientation, such as or use in spinal fusion cases or other spinal or bone applications, where a controllable spacer is needed. The device can be made of any medical material compatible for bone utilization, such as but not limited to, titanium or titanium alloy, PEEK (polyether ether ketone), polymers, resorbable materials or any other metal, natural or synthetic material or combinations of them. The surfaces of the device may be regular or irregular, including surfaces that may enhance attachment with bone. The device may have superior and inferior surfaces parallel or tilted to suit any intervertebral space shape.

In general, the device includes a cage made of at least two segments, each one having a bone graft cavity or chamber, and an instrument for manipulation of the cage. The instrument fits any of the different embodiments described herein. Each embodiment has a different way of controlling and/or locking the movement of the segments relative to each other.

There is thus provided in accordance with a non-limiting embodiment of the present invention a cage device including first and second segments pivotally connected by a hinge, wherein pivoted movement of the segments with respect to each other is limited by a first stopper portion of the first segment abutting against a second stopper portion of the second segment.

In accordance with a non-limiting embodiment of the present invention the first and second segments are formed with bone graft chambers.

In accordance with a non-limiting embodiment of the present invention the hinge includes an eccentric hinge.

In accordance with a non-limiting embodiment of the present invention the hinge includes mating ratchet teeth.

In accordance with a non-limiting embodiment of the present invention the hinge includes a detent mechanism.

In accordance with a non-limiting embodiment of the present invention a pushing element is operative to push one of the segments relative to the other segment. The pushing element may be centered with respect to the hinge. The pushing element is off-center with respect to the hinge.

In accordance with a non-limiting embodiment of the present invention the hinge includes a variable center of rotation.

In accordance with a non-limiting embodiment of the present invention the cage device includes a tool for manipulating the segments.

BRIEF DESCRIPTION OF THE DRAWINGS

The present invention will be understood and appreciated more fully from the following detailed description taken in conjunction with the drawing in which:

FIGS. 8A-8C are simplified illustrations of one type of tool for inserting and manipulating any of the cage devices of the invention.

DETAILED DESCRIPTION OF EMBODIMENTS

Figure 1A:
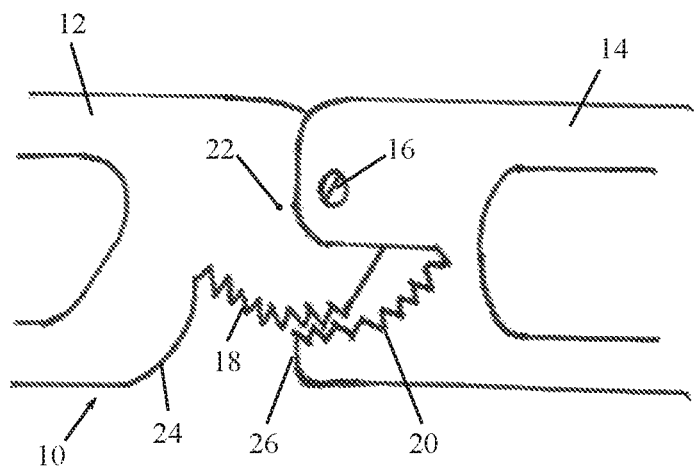
FIG. 1A-1B is a simplified illustration of a cage device, constructed and operative in accordance with a non-limiting embodiment of the present invention.
Figure 1B:
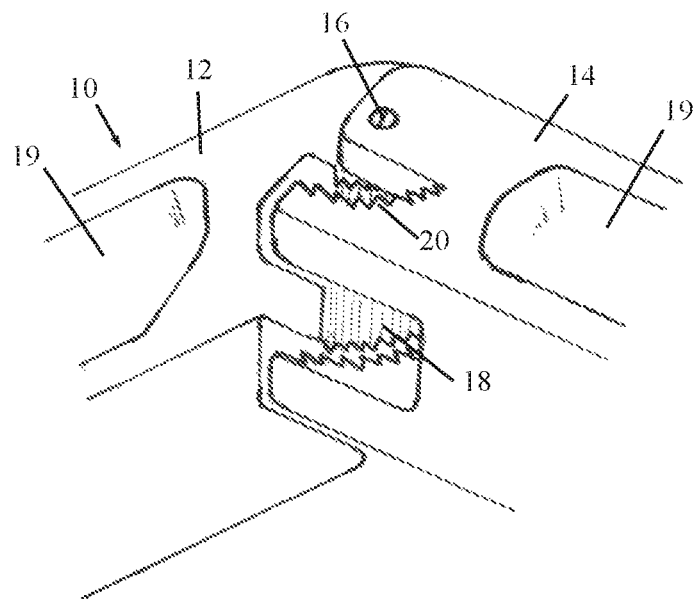

Reference is now made to FIGS. 1A-1B, which illustrate a cage device 10, in accordance with a non-limiting embodiment of the present invention.

Cage device 10 includes first and second segments 12 and 14 connected by an eccentric hinge 16. The first and second segments 12 and 14 are formed with cooperating first and second ratchets 18 and 20, respectively, which ratchet together as first segment 12 pivots about hinge 16 relative to second segment 14. The hinge 16 is eccentric, which means the pivot point of the hinge is off-center from the center point 22 of the first ratchet 18, that is, the origin of the radius of curvature of the curved contour on which the ratchet teeth are formed. The segments can be steered in one direction in controlled steps per the teeth spacing of the ratchet system, until reaching a final limit when a first stopper portion 24 of first segment 12 abuts against a second stopper portion 26 of second segment 14. The segments may include bone graft chambers 19.

Figures 2A, 2B:
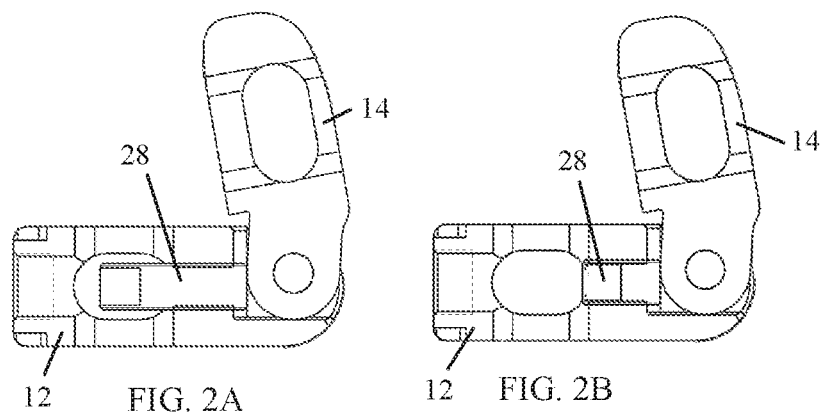
FIGS. 2A-2B are simplified illustrations of steering first and second segments of the cage device.

Reference is now made to FIGS. 2A-2B. The first and second segments 12 and 14 are steered or pivoted relative to each other by a pushing element 28, such as a locking screw or pin (long or short, centered or not) that can be manipulated from the outside by an insertion instrument (not shown), such as a screwdriver or rod, for control and locking the device in a final angulated (pivoted) position. Without limitation, FIGS. 2A and 2B show two different possible lengths of pushing elements 28.

Figures 3A, 3B:
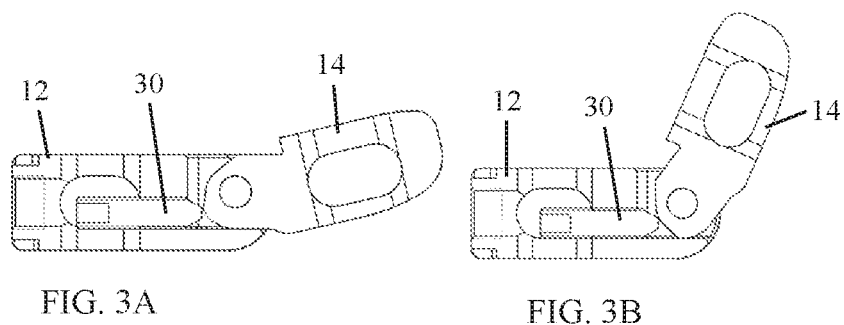
FIGS. 3A-3C are simplified illustrations of a pushing element for controlled pivoting movements of the segment.
Figure 3C:
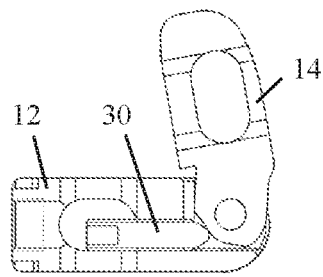

Reference is now made to FIGS. 3A-3C. Controlled pivoting movements of the distal segment 14 can be achieved by using a pushing element 30 (e.g., screw) with offset positioning in the proximal segment 12. Alternatively, in another embodiment, the pushing element 30 and the surface of the pivot point corresponding to the distal segment 14 can have a transmission mechanism that causes the movement, such as a link, gear and the like.

Figure 4A:
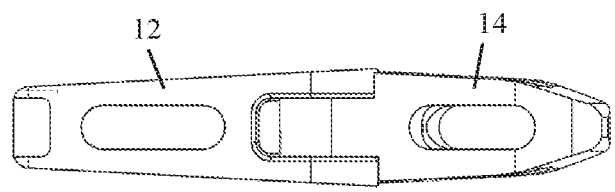
FIGS. 4A-4D are simplified illustrations of the segments of the cage device with different sloped and straight surfaces.
Figure 4B:
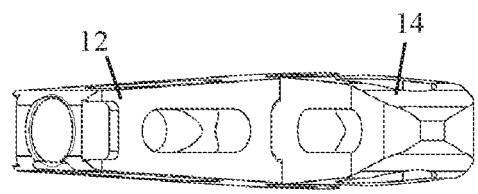
Figure 4C:
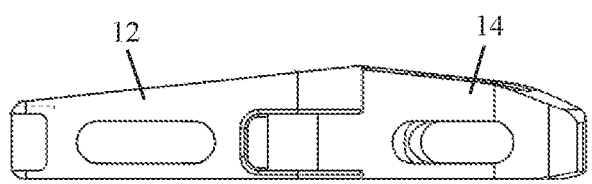
Figure 4D:
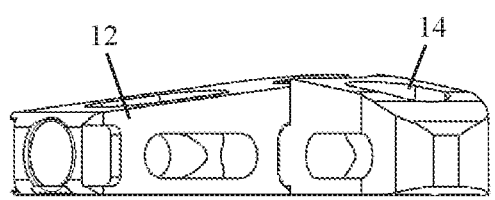

Reference is now made to FIGS. 4A-4D. In FIGS. 4A and 4B (FIG. 4B shows distal segment 14 tilted with respect to proximal segment 12), both segments have sloped upper and lower surfaces. The distal segment 14 has a tapered distal nose portion. In FIGS. 4C and 4D (FIG. 4D shows distal segment 14 tilted with respect to proximal segment 12), both segments have sloped upper surfaces but horizontal lower surfaces. In general, the device of the invention can have a symmetrical or a non-symmetrical shape, with parallel or angled contact surfaces.

Figure 5A:
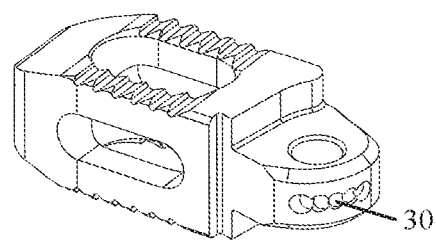
FIGS. 5A-5C are simplified illustrations of a detent mechanism that controls and locks the pivoting segments of a cage device.
Figure 5B:
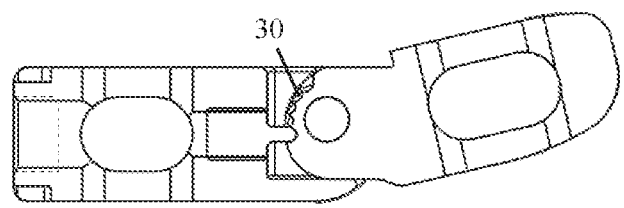
Figure 5C:
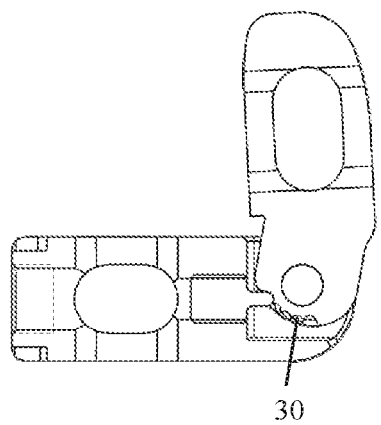

Reference is now made to FIGS. 5A-5C. In this embodiment, instead of a ratchet, a detent mechanism 30 controls and locks the pivoting segments of the cage. The detent mechanism 30 is radially disposed around the rotating point 16. The detent mechanism 30 is also manipulated through an insertion instrument (not shown) during insertion and positioning.

Figure 6A:
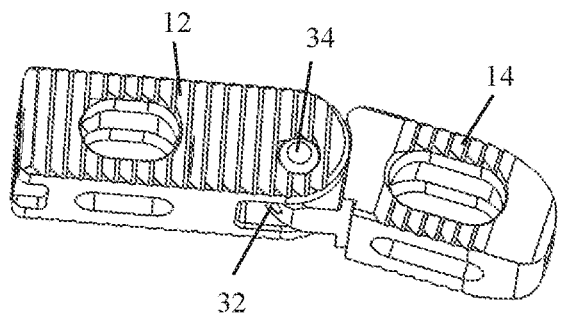
FIGS. 6A-6C are simplified illustrations of a cage device wherein the segments are connected by a ratcheted central hinge.
Figure 6B:
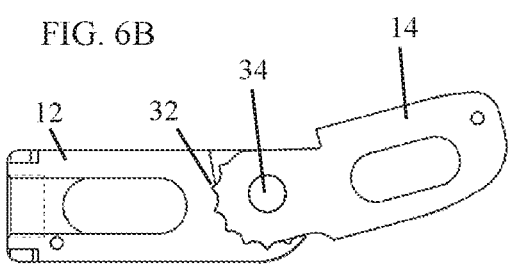
Figure 6C:
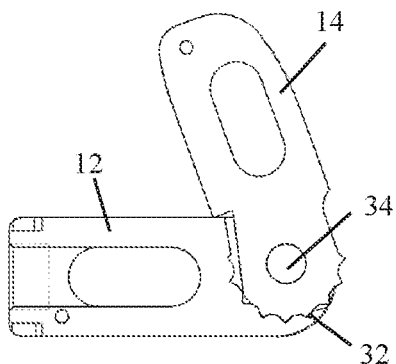

Reference is now made to FIGS. 6A-6C. This embodiment is similar to the embodiment of FIGS. 1A-1B, except that the first and second segments 12 and 14 are connected by a ratcheted central hinge 32 positioned at the rotating point 34 of the device.

Figure 7A:
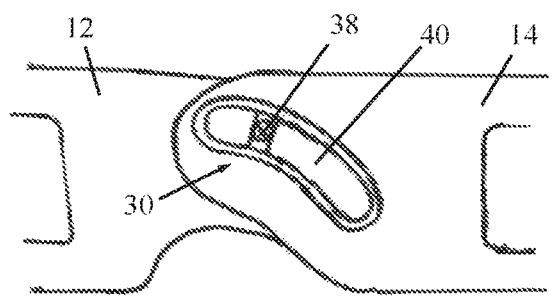
FIGS. 7A-7B are simplified illustrations of a cage device wherein the segments are connected by a hinge that has a variable center of rotation.
Figure 7B:
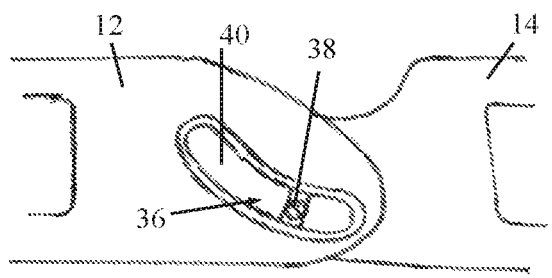

Reference is now made to FIGS. 7A-7B. In this embodiment, the first and second segments 12 and 14 are pivotally connected by a hinge 36 that has a variable center of rotation. Hinge 36 includes a pin 38 that slides in an arcuate groove 40; the position of the pin 38 in the groove 40 determines the rotating point of the two segments. This increases the manipulation possibilities of the cage.

Reference is now made to FIGS. 8A-8C, which illustrate one type of instrument or tool 50 for inserting and manipulating any of the cage devices of the invention. The tool 50 is described in U.S. patent application Ser. No. 14/754,727, the disclosure of which is incorporated herein by reference. Briefly, at the beginning of the procedure, the tool 50 is attached to the cage 10 and a distal limiter 52 is used to limit articulation of the cage segments 12 and 14, so that it is easier to insert the cage into the patient. During insertion, the articulation is controlled by the distal limiter 52. The distal limiter 52 can be connected to the cage 10 so as to actively steer the segments.

What is claimed is:

1. A cage device comprising:
   first and second segments pivotally connected by a hinge, wherein pivoted movement of said segments with respect to each other is limited by a first stopper portion of said first segment abutting against a second stopper portion of said second segment,
   wherein said first segment and said second segment have mating ratchet teeth extending along arcs, the first and second segments being pivotable about the hinge in controlled steps per the teeth spacing of the mating ratchet teeth,
   wherein the hinge has a pivot point that is off-center from the arcs along which the mating ratchet teeth extend.

2. The cage device according to claim 1, wherein said first and second segments are formed with bone graft chambers.

3. The cage device according to claim 1, further comprising a pushing element operative to push one of the segments relative to the other segment for controlled pivoting of the first and second segments relative to one another.

4. The cage device according to claim 3, wherein said pushing element is centered with respect to said hinge.

5. The cage device according to claim 3, wherein said pushing element is off-center with respect to said hinge.

6. The cage device according to claim 3, wherein the pushing element is operatively coupled to the first segment and configured to translate relative to the first segment.

7. The cage device according to claim 6, wherein the pushing element comprises a screw.

8. The cage device according to claim 1, wherein said hinge comprises a variable center of rotation.

9. The cage device according to claim 1, comprising a tool for manipulating the segments.

* * * * *